US008945631B2

(12) United States Patent
Masaoka et al.

(10) Patent No.: US 8,945,631 B2
(45) Date of Patent: Feb. 3, 2015

(54) LIQUID FOR TREATMENT OF CITRUS GREENING DISEASE AND TREATMENT METHOD USING SAME

(75) Inventors: Yoshikuni Masaoka, Hiroshima (JP); Makoto Usui, Aichi (JP); Tomoya Matsuyama, Aichi (JP)

(73) Assignees: Hiroshima University, Hiroshima (JP); Aichi Steel Corporation, Aichi (JP)

( * ) Notice: Subject to any disclaimer, the term of this patent is extended or adjusted under 35 U.S.C. 154(b) by 0 days.

(21) Appl. No.: 13/994,076

(22) PCT Filed: Dec. 1, 2011

(86) PCT No.: PCT/JP2011/077868

§ 371 (c)(1), (2), (4) Date: Jun. 13, 2013

(87) PCT Pub. No.: WO2012/081420

PCT Pub. Date: Jun. 21, 2012

(65) Prior Publication Data

US 2013/0259954 A1 Oct. 3, 2013

(30) Foreign Application Priority Data

Dec. 14, 2010 (JP) ................................ 2010-278654

(51) Int. Cl.
*A01N 59/16* (2006.01)
*A01N 55/02* (2006.01)
*A01N 37/44* (2006.01)

(52) U.S. Cl.
CPC ................ *A01N 59/16* (2013.01); *A01N 37/44* (2013.01)
USPC .......................................... 424/648; 514/502

(58) Field of Classification Search
USPC .......................................... 424/648; 514/502
See application file for complete search history.

(56) References Cited

U.S. PATENT DOCUMENTS 2,822,317 A * 2/1958 Gulesich et al. .............. 424/648
6,306,201 B1 * 10/2001 Makino ...................... 106/14.13

FOREIGN PATENT DOCUMENTS

JP 2000-044417 2/2000
JP 2006267092 A * 10/2006
JP 2007-137791 6/2007
WO 2012/081420 A1 6/2012

OTHER PUBLICATIONS

Leonard, C.D., Use of Dimethyl Sulfoxide as a Carrier for Iron in Nutritional Foliar Sprays Applied to Citrus, 1967, Annals New York Academy of Sciences, pp. 148-158.*

Polek, Marylou, et al. Citrus Bacterial Canker Disease and Huanglongbing (Citrus Greening), 2007, University of California Division of Agriculture and Natural Resources, Publication 8218, pp. 1-12.*

Masaoka, T., Method and Kit for Detecting Citrus Greening Disease, 2006, JP 2006-267092, Abstract, 2 pages.*

* cited by examiner

*Primary Examiner* — Abigail Fisher
*Assistant Examiner* — Andriae M Holt
(74) *Attorney, Agent, or Firm* — K&L Gates LLP; Louis C. Cullman; Michelle Glasky Bergman

(57) ABSTRACT

Provided are: a liquid for treatment of Citrus greening disease, which is capable of curing citrus trees with Citrus greening disease; and a treatment method using the liquid. The liquid for treatment of Citrus greening disease contains Fe ions and at least some of the Fe ions are present in the form of $Fe^{2+}$ ions. This treatment liquid contains a predetermined amount of Fe ions and an acid. Citrus greening disease is able to be cured by spraying the treatment liquid onto leaves of citrus trees infected with Citrus greening disease or by pouring the treatment liquid on the roots of citrus trees infected with Citrus greening disease.

7 Claims, 10 Drawing Sheets

LIQUID FOR TREATMENT OF CITRUS GREENING DISEASE AND TREATMENT METHOD USING SAME

TECHNICAL FIELD

The present invention relates to a liquid for treatment of Citrus greening disease and a treatment method using the liquid.

BACKGROUND ART

Citrus greening disease (Huanglongbing: hereinafter also referred to as HLB disease) is one of the most important diseases of citrus. HLB disease is a plant disease that is caused by infection of HLB bacteria to a tree such as a citrus tree.

The size of citrus fruits with HLB disease is small; the great parts of citrus fruits with HLB disease remain green even when the fruits are ripe; and the taste of citrus fruits with HLB disease is quite bitter. Therefore, citrus fruits with HLB disease have little commercial value. In addition, trees with HLB disease will lose their leaves, and will wither and die before long. Hence, HLB disease is a serious disease that causes heavy damage to horticulture and agriculture.

At the present time, early discovery and cutting of diseased trees, and control of Diaphorina citri, an insect vector, are considered to be the best as a method to deal with HLB disease. As a method for discovering HLB disease, Patent Literature 1 discloses a method and a kit for detecting Citrus greening disease.

CITATION LIST

Patent Literature

Patent Literature 1: Unexamined Japanese Patent Application Kokai Publication No. 2006-267092

SUMMARY OF INVENTION

Technical Problem

The invention of Patent Literature 1 allowed a simplified detection of a tree with HLB disease, but the tree with HLB disease had to be cut down.

The present invention has been made in view of the above-described matters, and an objective of the present invention is to provide a liquid for treatment of Citrus greening disease, which is capable of curing citrus trees with Citrus greening disease, and a treatment method using the liquid.

Solution to Problem

The liquid for treatment of Citrus greening disease according to the first mode of the present invention, wherein the liquid contains Fe ions and at least some of the Fe ions are $Fe^{2+}$ ions.

It is preferable that the concentration of total Fe ions be from 10 mg/L to 100 mg/L.

In addition, it is preferable that the treatment liquid further contain an acid in addition to the total Fe ions.

In addition, it is preferable that the acid be an organic acid.

In addition, it is preferable that the organic acid comprise at least one of a carboxyl group and a hydroxyl group, and the total number of the carboxyl groups and the hydroxyl groups in the acid be two or more.

In addition, it is preferable that the organic acid be at least one of citric acid, malic acid, tartaric acid and ascorbic acid.

It is preferable that a plant, to which the treatment liquid is applied, be a citrus plant.

It is preferable that a plant, to which the treatment liquid is applied, be rough lemon, tankan orange or shekwasha.

The method for treatment of Citrus greening disease according to the second mode of the present invention, wherein Citrus greening disease is cured by applying the treatment liquid according to any one of the above to leaves, the rhizosphere, or both of leaves and the rhizosphere, of a citrus plant infected with Citrus greening disease to decrease or vanish pathogenic bacteria in the citrus plant.

Advantageous Effects of Invention

Citrus greening disease is able to be cured by applying the liquid for treatment of Citrus greening disease according to the present invention to a tree with Citrus greening disease, and the tree does not have to be cut down.

Figure 1:
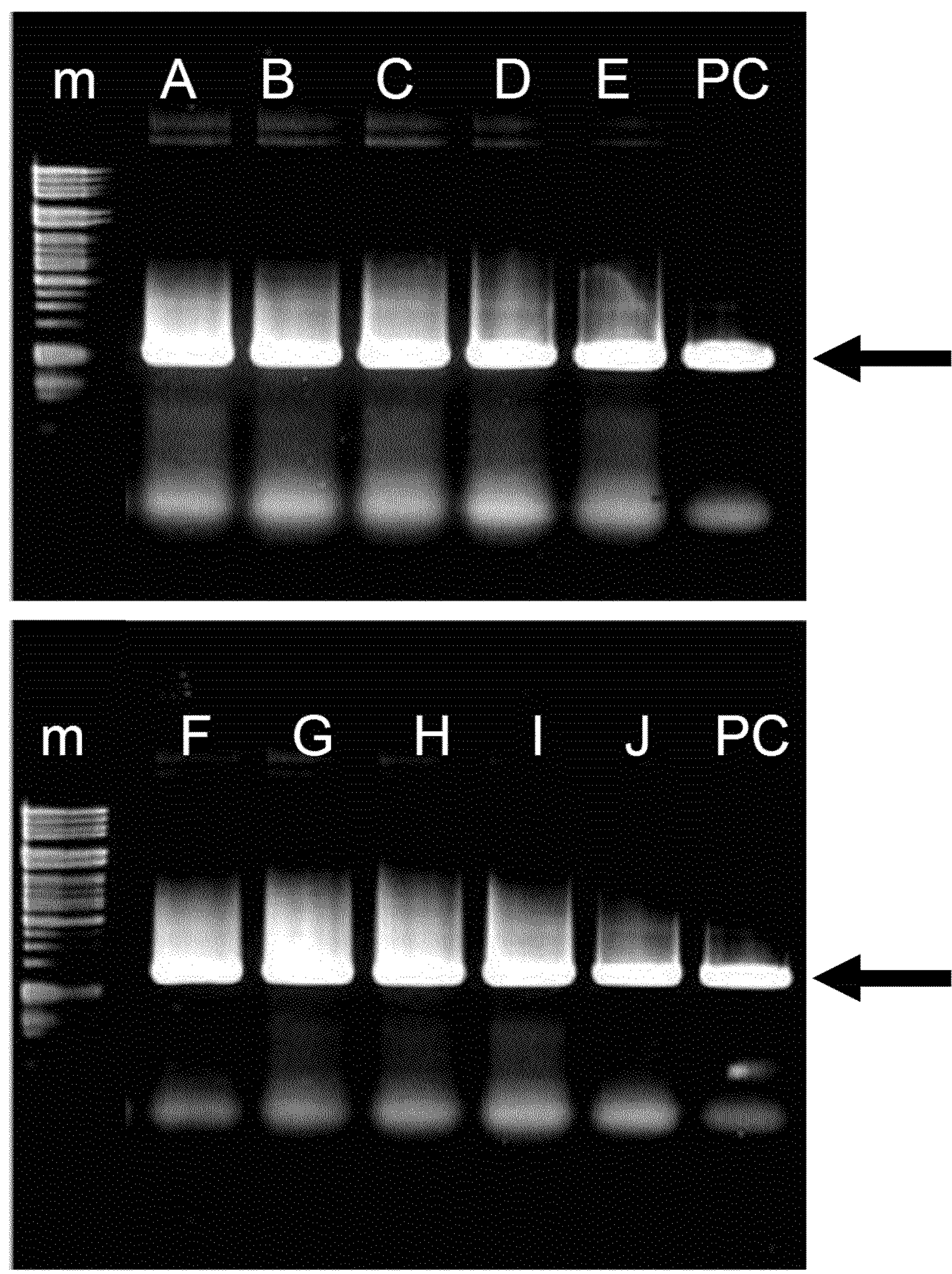
FIG. 1 shows the results of PCR diagnosis of specimens to which an aqueous Fe-EDTA solution was applied.

DESCRIPTION OF EMBODIMENTS (Liquid for Treatment of Citrus Greening Disease)

The liquid for treatment of Citrus greening disease (hereinafter also referred to simply as the "treatment liquid") according to this embodiment contains $Fe^{2+}$ ions. This treatment liquid stably holds $Fe^{2+}$ ions.

The treatment liquid according to this embodiment is able to be obtained by dissolving in water an iron compound capable of supplying $Fe^{2+}$ ions. In the treatment liquid according to this embodiment, the iron compounds capable of supplying $Fe^{2+}$ ions are not particularly limited, as long as the iron compounds are capable of containing $Fe^{2+}$ ions in an aqueous solution. For example, it is possible to use a ferrous iron compound such as FeO or $FeSO_4$. In addition, it is possible to use an iron compound that comprises ferric iron in the form of powder, such as iron citrate, as long as the iron compound is capable of containing $Fe^{2+}$ ions in an aqueous solution through the equilibrium between $Fe^{3+}$ ions and $Fe^{2+}$ ions when the compound is dissolved in water.

The concentration of total Fe ions contained in the treatment liquid according to this embodiment is preferably from 10 mg/L to 100 mg/L, more preferably from 12 mg/L to 50 mg/L, still more preferably from 15 mg/L to 30 mg/L. If the concentration is lower than 10 mg/L, a sufficient therapeutic effect on HLB disease is not able to be obtained. If the concentration is higher than 100 mg/L, there is a possibility that a tree with HLB disease itself is damaged. In general, when iron is applied as a nutrient ingredient to a plant, a concentration range of from 1 to 1.5 mg/L is used. On the other hand, the treatment liquid according to this embodiment exhibits an excellent effect in curing HLB disease by the inclusion of total Fe ions in a high concentration of from 10 to 100 mg/L.

In the present specification, the "total Fe ions" include ferrous iron ions ($Fe^{2+}$ ions) and ferric iron ions ($Fe^{3+}$ ions).

The concentration of $Fe^{2+}$ ions is able to be measured by an existing method such as a method using o-phenanthroline. Since o-phenanthroline selectively forms complexes with $Fe^{2+}$ ions, it is possible to selectively quantify $Fe^{2+}$ ions by measuring the absorbance of the complexes. In addition, the amount of total Fe ions is able to be quantified by reducing in advance $Fe^{3+}$ ions contained in a solution to convert all Fe ions into ferrous irons and thereafter carrying out quantification using an o-phenanthroline method.

In general, $Fe^{2+}$ ions are easily converted into $Fe^{3+}$ ions by oxidation, but, on the other hand, the treatment liquid according to this embodiment is capable of stably holding $Fe^{2+}$ ions by preferably containing an acid. As an acid contained in the treatment liquid, any of an organic acid and an inorganic acid is able to be used, as long as the acid is capable of stably holding $Fe^{2+}$ ions. An organic acid is preferable, because $Fe^{2+}$ ions are to be more stably held.

The organic acid is an acid which comprises a carboxyl group and/or a hydroxyl group and in which the total number of the carboxyl groups and the hydroxyl groups is two or more, and forms chelates, in water, with $Fe^{2+}$ ions generated from an iron compound as mentioned above. Thereby, $Fe^{2+}$ ions stably exist in water. Examples of organic acids comprising carboxyl groups include citric acid (anhydrous citric acid), malic acid, tartaric acid, oxalic acid and the like. Examples of organic acids comprising hydroxyl groups include ascorbic acid and the like. Examples of organic acids comprising both of carboxyl groups and hydroxyl groups include citric acid, malic acid, tartaric acid and the like. It is possible to use only one of these organic acids, and it is also possible to use in combination two or more of these organic acids.

Among these organic acids, citric acid, malic acid, tartaric acid or ascorbic acid is preferable because of their excellent stability of $Fe^{2+}$ ions in the treatment liquid. Further, citric acid or tartaric acid is more preferable because of their high concentrations of $Fe^{2+}$ ions relative to the concentrations of the organic acids in cases of preparing aqueous solutions that contain these organic acids and iron compounds. Of citric acid and tartaric acid, citric acid is most preferable because of its particularly high concentration of $Fe^{2+}$ ions relative to the concentration of the organic acid in cases of preparing an aqueous solution that contains the organic acid and an iron compound. In addition, citric acid is also an organic acid produced by citruses themselves, and therefore does not harm the citruses.

Water to be used for the treatment liquid is not particularly limited, and various kinds of water are able to be used. It is possible to use highly purified water such as pure water or ion exchanged water, and it is also possible to use generally-used water such as tap water, industrial water, agricultural water or underground water.

Furthermore, in addition to the organic acid and the iron compound, other nutrient ingredient such as magnesium, calcium or the like is allowed to be contained in the treatment liquid.

In addition, the treatment liquid according to this embodiment is also able to be obtained by the production methods as described below.

The treatment liquid is able to be obtained by dissolving in water an organic acid powder and an iron compound powder capable of supplying $Fe^{2+}$ ions while heating.

In addition, the treatment liquid is also able to be obtained by dissolving in advance the total amount of the organic acid powder in water to obtain an aqueous organic acid solution, adding to the aqueous organic acid solution an iron compound powder that supplies $Fe^{2+}$ ions, and heating the resulting solution.

In addition, the treatment liquid is also able to be obtained by adding to water a powder of ferrous organic acid such as ferrous citrate and heating the resulting solution.

In addition, the treatment liquid is also able to be obtained by mixing an organic acid powder, an iron compound powder that supplies $Fe^{2+}$ ions, and water without heating.

The treatment liquid according to this embodiment is capable of curing HLB disease by application of the treatment liquid to citrus trees with HLB disease. Citruses include, for example, rough lemon (*Citrus verrucosa*), tankan orange (*Citrus tankan*), shekwasha (*Citrus depressa* Hayata), satsuma orange (*Citrus unshiu*) and the like. Among these citruses, rough lemon (*Citrus verrucosa*), tankan orange (*Citrus tankan*) or shekwasha (*Citrus depressa* Hayata) is especially preferable.

HLB bacteria are phloem-localized and unculturable, various Gram-negative bacteria-like microorganisms, and are classified into three strains which are respectively called Asian type, African type and American type, and, in other words, are classified into three strains of *Candidatus Liberobacter asiaticus, Candidatus Liberobacter africanus* and *Candidatus Liberobacter americanus*, respectively. The treatment liquid according to this embodiment is able to be used against infection by HLB bacteria of any of the three strains.

The application of the treatment liquid is able to be performed by, for example, spraying onto leaves of a tree or pouring on the roots of a tree, that is, on the rhizosphere.

The frequency of the application of the treatment liquid to a citrus tree and the amount of the treatment liquid to be applied at one time are not particularly limited. As an example, it is possible to cure a citrus tree with Citrus greening disease by applying 50 mL of the treatment liquid having an $Fe^{2+}$ ion concentration of from 15 mg/L to 50 mg/L once every 5 days as described in the Examples below.

Although the mechanism of curing Citrus greening disease is uncertain, it is assumed that hydroxy radicals, which are generated by the treatment liquid applied to a tree, influence the mechanism as explained in the Examples below.

In general, it is known that active oxygen is involved in the resistance of cells to an invader such as a pathogen. Within a cell, the active oxygen serves to protect the cell from pathogenic stress, and the concentration of the active oxygen within the cell is regulated through Fenton reaction in which a hydrogen peroxide generated within the cell reacts with a ferrous iron to generate a hydroxy radical.

The treatment liquid according to this embodiment is capable of stably holding $Fe^{2+}$ ions and continuously generating hydroxy radicals as demonstrated in the Examples below. Therefore, it is thought that, when the treatment liquid is applied to a tree, highly reactive hydroxy radicals are generated within the cells of the citrus, and the hydroxy radicals directly kill HLB bacteria or kill HLB bacterium by a secondary action through prompting any reactivity within the cells, thereby allowing Citrus greening disease to be cured.

In addition, it has been found that iron in a citrus tree with Citrus greening disease is decreased as compared to iron in a normal tree. In general, plants take in $Fe^{2+}$ ions from the roots through reduction of $Fe^{3+}$ ions. However, in case of the treatment liquid according to this embodiment, the treatment liquid is an aqueous solution in which $Fe^{2+}$ ions stably exist, and therefore plants are able to take in $Fe^{2+}$ ions as they are. In addition, it is also possible to think that the treatment liquid contains a large number of $Fe^{2+}$ ions, and citrus trees are therefore able to directly take in many $Fe^{2+}$ ions and supplement the deficiency of iron, thereby allowing enhancement of the therapeutic effect.

EXAMPLES

Preparation of Aqueous Fe Solutions for Tests

The following aqueous Fe solutions for tests were respectively prepared.

1. An aqueous Fe-EDTA solution
2. Treatment Liquid A (an aqueous solution)
3. Treatment Liquid B (an aqueous solution)
4. An aqueous iron citrate solution
5. An aqueous iron sulfate solution (1. An Aqueous Fe-EDTA Solution)

An aqueous Fe-EDTA solution was prepared by dissolving Fe-EDTA (manufactured by Sigma-Aldrich Japan, trade name: sodium ethylenediamine tetraacetate (III)) with desalted distilled water such that the concentration of total Fe ions is 15 mg/L.

(2. Treatment Liquid A (an Aqueous Solution))

Treatment Liquid A was prepared by diluting a Treatment Liquid A stock solution, which contains 14 g of citric acid per 100 mL of water and 40 parts by mass of Fe per 100 mL of water when taking the content of citric acid as 100 parts by mass, with desalted distilled water such that the concentration of total Fe ions is 15 mg/L.

The aqueous solution obtained by diluting the Treatment Liquid A stock solution contains $Fe^{2+}$ ions and $Fe^{3+}$ ions, and the $Fe^{2+}$ ions are from 20 to 40% by mass when taking the total amount of the $Fe^{2+}$ ions and the $Fe^{3+}$ ions as 100% by mass. However, the values of these ion concentrations are those that were measured by the measurement methods as described below.

(3. Treatment Liquid B (an Aqueous Solution))

Treatment Liquid B was prepared by diluting a Treatment Liquid B stock solution, which contains 14 g of citric acid per 100 mL of water and 13 parts by mass of Fe per 100 mL of water when taking the content of citric acid as 100 parts by mass, with desalted distilled water such that the concentration of total Fe ions is 15 mg/L.

The aqueous solution obtained by diluting the Treatment Liquid B stock solution contains $Fe^{2+}$ ions and $Fe^{3+}$ ions, and the $Fe^{2+}$ ions are from 50 to 90% by mass when taking the total amount of the $Fe^{2+}$ ions and the $Fe^{3+}$ ions as 100% by mass. However, the values of these ion concentrations are those that were measured by the measurement methods as described below.

(4. An Aqueous Iron Citrate Solution)

An aqueous iron citrate solution was prepared by dissolving iron citrate (Showa Kako Corporation) with desalted distilled water such that the concentration of total Fe ions is 15 mg/L.

(5. An Aqueous Iron Sulfate Solution)

An aqueous iron sulfate solution was prepared by dissolving iron sulfate with desalted distilled water such that the concentration of total Fe ions is 15 mg/L.

(Measurements of the Concentrations of Total Fe Ions)

In order to confirm the $Fe^{2+}$ ions contained in Treatment Liquid A, Treatment Liquid B, the aqueous iron citrate solution, the aqueous Fe-EDTA solution or the aqueous iron sulfate solution, the concentrations of $Fe^{2+}$ ions in these aqueous Fe solutions were measured. These measurements were carried out using aqueous Fe solutions which had been prepared such that the concentrations of total Fe ions are about 50 mg/L.

First, a Treatment Liquid A aqueous solution was prepared in the same manner as described above by diluting the Treatment Liquid A stock solution with ion exchanged water such that the concentration of total Fe ions is about 50 mg/L Immediately thereafter, the $Fe^{2+}$ ions and the total Fe ions contained in the obtained aqueous solution were measured using RQflex multi-parameter water quality analyzer (manufactured by Merck Ltd.) and Reflectoquant iron ion test strips (manufactured by Merck Ltd.). The measurements were carried out according to the protocol attached to the Reflectoquant iron ion test strips. In addition, the amount obtained by subtracting the amount of $Fe^{2+}$ ions from the amount of total Fe ions was calculated as the amount of $Fe^{3+}$ ions. These measurements were carried out in a room in which no direct sunlight comes in at all times.

According to the results of these measurements, the concentration of $Fe^{2+}$ ions was 10.4 mg/L; the concentration of $Fe^{3+}$ ions was 36.6 mg/L; and, when taking the total of the $Fe^{2+}$ ions and the $Fe^{3+}$ ions as 100% by mass, the $Fe^{2+}$ ions were 22% by mass.

A Treatment Liquid B aqueous solution, an aqueous iron citrate solution, an aqueous Fe-EDTA solution and an aqueous iron sulfate solution were respectively prepared in the same manner as described above such that the concentrations of total Fe ions are about 50 mg/L, and the concentrations of $Fe^{2+}$ ions, the concentrations of total Fe ions, and the proportions of $Fe^{2+}$ ions in the total Fe ions, in these aqueous solutions were measured. The results are shown in Table 1.

TABLE 1

| | Treatment Liquid A | Treatment Liquid B | iron citrate | Fe-EDTA | iron sulfate |
|---|---|---|---|---|---|
| Concentration of $Fe^{2+}$ ions (mg/L) | 10.4 | 42 | 6.8 | 0 | 42 |
| Concentration of total Fe ions (mg/L) | 47 | 44 | 38 | 43 | 41 |
| Proportion of $Fe^{2+}$ions (%) | 22% | 95% | 18% | 0% | 100% |

Thus, it was confirmed that the Treatment Liquid A aqueous solution, the Treatment Liquid B aqueous solution, the aqueous iron citrate solution and the aqueous iron sulfate solution all contain $Fe^{2+}$ ions in the given proportions. On the other hand, it was confirmed that the aqueous Fe-EDTA solution stably holds $Fe^{3+}$ ions.

(Verification of Therapeutic Effect on Citrus Greening Disease)

The aqueous Fe solutions described above were applied to citrus trees infected with Citrus greening disease to verify the therapeutic effect of the treatment liquids containing $Fe^{2+}$ ions on Citrus greening disease.

1. Effect on Rough Lemon

A tree of rough lemon (*Citrus verrucosa* Lush.) was used as a specimen. First, a seed of rough lemon was germinated and grown using an about 1-L pot and soil for raising vegetable seedlings (manufactured by TAKII & Co., Ltd.). One year after the growing, the specimen was infected with Citrus greening disease by allowing the specimen to take in the pathogenic bacteria from a pathogenic tree by grafting. The pathogenic tree was a tree infected with a pathogenic bacterial strain that had been collected in Ishigaki Island and named "Ishi-1". After the infection, the specimen which had been grown for another 1 year was subjected to the tests. In the same manner, 10 specimens infected with Citrus greening disease (Specimens A to J) were prepared.

The cultivation was carried out in a growth cabinet. The cultivation was carried out under the conditions a daytime temperature of 32° C. and a night temperature of 28° C. Nutrients were applied to the soil every 10 days. The applied nutrients were an aqueous solution that contains 10 mM calcium nitrate, 2.5 mM monopotassium dihydrogen phosphate, 2.5 mM magnesium sulfate heptahydrate and 1 mM potassium sulfate, and the solution was applied in an amount of 50 mL/one time per 1 pot.

1-1. Application of Aqueous Fe-EDTA Solution

The 10 specimens (Specimens A to J) prepared as described above were grown. First, the aqueous Fe-EDTA solution whose concentration of total Fe ions is 15 mg/L was applied to 5 specimens (Specimens A to E) until Day 60; and, instead of the aqueous Fe-EDTA solution, distilled water was applied to the other 5 specimens (Specimens F to J).

The above application of the aqueous Fe-EDTA solution and distilled water was carried out by spraying onto the leaves of the specimens and pouring on the roots of the specimens. The spraying onto the leaves and the pouring on the roots were respectively carried out once every 5 days. The amounts of the aqueous Fe-EDTA solution and distilled water that were sprayed onto the leaves are each 50 mL per one time. Moreover, the amounts of the aqueous Fe-EDTA solution and distilled water that were poured on the roots are each 50 mL per one time.

On Day 60 after the beginning of the treatment of the aqueous Fe-EDTA solution (Day 60 of the growing), about 3 to 5 leaves of each specimen were picked, and the DNAs were extracted and amplified by a PCR method, followed by carrying out a diagnosis (hereinafter referred to as the PCR diagnosis) for Citrus greening disease. Specifically, the extraction and the diagnosis were carried out as follow.

(1) DNA Extraction

The collected leaves (3 to 5 g) were washed with distilled water; the water was removed; midribs were cut off; and thereafter the resultants were frozen using liquid nitrogen. The resulting substances were homogenized using a mortar and a pestle that had been steam sterilized and dry heat sterilized; the homogenates were dissolved in 5 mL of 1×CTAB buffer (1% CTAB, 50 mM Tris-HCl (pH 8.0), 0.7 M NaCl, 10 mM EDTA); the resulting solution was incubated for 30 minutes at 65° C. while stirring; thereafter, 5 mL of chloroform and isoamyl alcohol (24:1 v/v) was added; the obtained mixture was mixed by inversion for 30 minutes and centrifuged at 3000 rpm for 15 minutes; and the supernatant was transferred to a new centrifuge tube using a dropper. The deproteinization treatment described above was carried out 3 times. A 10% CTAB solution (10% CTAB, 0.7 M NaCl) in an amount of one tenth of the supernatant was added and the resulting solution was mixed by inversion, followed by supplementing CTAB that had been lost through the deproteinization treatment described above. To the supernatant, an equal amount of a CTAB precipitation solution (1% CTAB, 50 mM Tris-HCl, pH 8.0, 0.10 mM EDTA) was slowly added, and the obtained solution was gently mixed by inversion. At a low concentration (NaCl of 0.35 M or less), nucleic acids present in the supernatant are bound to CTAB and precipitated. The resulting solution was left to stand overnight to allow nucleic acids to precipitate, and centrifuged at 1800 rpm for 15 minutes, and the supernatant containing starch was removed. To the precipitate, 1 mL of a precipitate-dissolving solution (1 M NaCl, 50 mM Tris-HCl, 10 mM EDTA) was added to separate the nucleic acid-CTAB complex and dissolve the nucleic acids. To this nucleic acid solution, an equal amount of isoamyl alcohol was slowly added to precipitate nucleic acids. The resulting solution was centrifuged at 1800 rpm for 10 minutes, and the supernatant containing CTAB was removed. Precipitation of nucleic acids and washing of CTAB on the inner wall of the centrifuge tube were carried out using 70% ethanol; centrifugation was performed in the same manner; and CTAB was removed. Finally, nucleic acids were dissolved with 1/10 TE solution (10 mM Tris-HCl, 1 mM EDTA). The purity of the nucleic acid solution was determined by evaluating the degree of starch contamination at 260 nm/230 nm and the degree of protein contamination at 260 nm/280 nm using a spectrophotometer, and nucleic acid solutions in which both the values are not less than 1.8 were used for the next experiment. In addition, nucleic acid solutions whose molecular weights are equal to or higher than λDNA (47.5 kb) in agarose electrophoresis were used for the next experiment. The amount of DNAs was measured with a fluorescence spectrophotometer.

(2) PCR Diagnosis

The PCR diagnosis was carried out according to the method described in "Marjorie A. Hoy, Ayyamperumal Jeyaprakash, and Ru Nguyen (2001), Long PCR is a sensitive Method for Detecting Liberobacter asiaticum in Parasitoids Undergoing Risk Assessment in Quarantine. Biological Control 22, 278-287".

Specifically, 1 μL of 48 mM $MgCl_2$, 10 μL of Takara Premix tag 2×PCR solution (Takara, Bio Inc., Shiga, Japan), 1 μL of 90 ng/μL forward primer MHO035, 1 μL of 90 ng/μL reverse primer MHO0354, 2 μL (20 ng) of the DNA sample extracted as described above, and 5 μL of sterile water were mixed to prepare 20 μL of a PCR reaction solution. The PCR reaction solution was set in DNA Thermal Cycler PTC-1148 (Bio-Rad Laboratories, Inc.), and DNAs were amplified under the following conditions.

Primers

```
Forward Primer (MHO0353):
                                    (SEQ ID NO: 1)
5'-CACCGAAGATATGGACAACA-3'

Reverse Primer (MHO0354):
                                    (SEQ ID NO: 2)
5'-CAGGTTCTTGTGGTTTTTCTG-3'
```

PCR Conditions

90° C. for 3 minutes, 1 cycle;

{94° C. for 1 minute, 68.5° C. for 1 minute, and 72° C. for 3 minutes}, 35 cycles;

72° C. for 3 minutes, 1 cycle; and

Store at 4° C. until electrophoresis

As a positive control (PC), a DNA sample that had been extracted by the above-described DNA extraction method from leaves picked from a pathogenic tree infected with the pathogenic bacterial strain Ishi-1 was used.

Using 0.8% agarose gel, 17 μL, of each sample after the amplification by the above-described PCR method was electrophoresed, and the amplified DNAs were detected by ethidium bromide staining.

The results of the PCR diagnosis of the specimens to which the aqueous Fe-EDTA solution was applied and the results of the PCR diagnosis of the specimens to which distilled water was applied are shown in FIG. 1 and Table 2. In the figure, m represents a lane in which a molecular weight marker had been electrophoresed.

As shown in FIG. 1, in the positive control (PC), a positive band was detected at the given position (indicated by the arrow in the figure). It is possible to judge as follows: if this positive band is detected, then the specimen is diseased with Citrus greening disease; and, if not detected, then the specimen is not diseased with Citrus greening disease. In addition, the band intensities of the individual specimens when taking the intensity of the positive band of PC as 100% are shown in Table 2.

The band intensities as the results of the electrophoresis were analyzed using ImageJ (an image processing program, NIH). First, the band spot of PC (the white region in the figure) was selected, and the brightness (strength) of the selected region was digitized. The strengths in the regions, which are in the band spots of the samples and whose areas are each equal to the area of the region selected as the band of PC, were also digitized. Next, the strength of the black part which is blank is also digitized in the same manner, and the values obtained by subtracting the numerical value of the strength of the black part from the numerical value of the strength of each band were determined as original numerical values of the bands. Table 2 shows relative values (%) of the original numerical values of the bands when taking the strength of the positive control (PC) as 100%.

TABLE 2

| | Specimen | | | | | | | | | | |
|---|---|---|---|---|---|---|---|---|---|---|---|
| | PC | A | B | C | D | E | F | G | H | I | J |
| Band intensity (%) | 100 | 101 | 101 | 101 | 126 | 84 | 101 | 101 | 101 | 126 | 84 |

Figure 8:
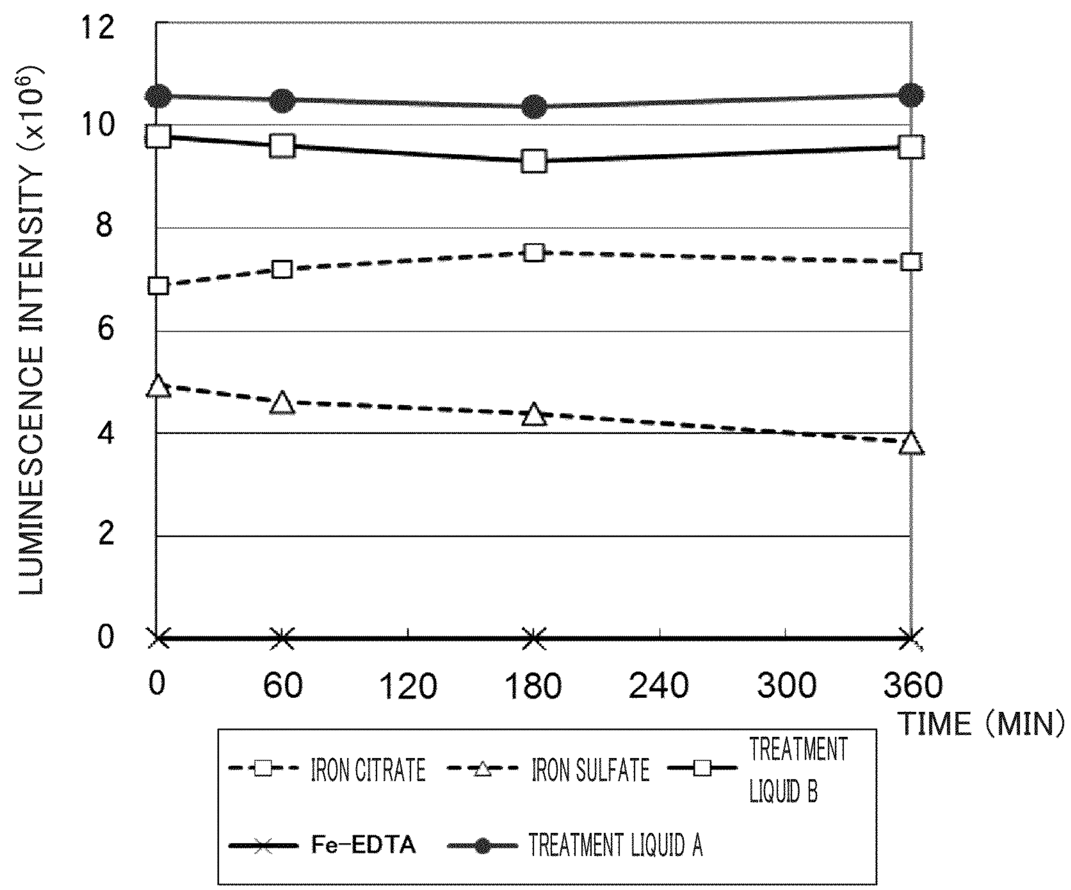
FIG. 8 shows the results obtained by measuring active oxygens by luminol reaction.

As a result, in all the specimens, bands appeared at the same position as in PC, and thereby it was revealed that HLB bacterial gene was present in the specimens. Therefore, these specimens all remained infected with HLB disease. Since the aqueous Fe-EDTA solution is an aqueous solution in which Fe is present in the form of $Fe^{3+}$ ions, it was revealed that, even if $Fe^{3+}$ ions are supplied, no effect of curing the specimens infected with HLB disease is observed. In addition, in the aqueous Fe-EDTA solution, the amount of active oxygens generated is markedly low as shown in FIG. 8 described below. Since active oxygens are hardly generated in case of the aqueous Fe-EDTA solution, it is assumed that the aqueous Fe-EDTA solution has no therapeutic effect on HLB disease.

1-2. Application of Treatment Liquid A

Also, after Day 61 of the growing, the specimens described above continued to be grown. After Day 61, instead of the aqueous Fe-EDTA solution, Treatment Liquid A was applied to the 5 specimens (Specimens A to E) at a concentration of total Fe ions of 15 mg/L.

The application of Treatment Liquid A was carried out, in the same manner as in the application of the aqueous Fe-EDTA solution, by spraying onto the leaves of the specimens and pouring on the roots of the specimens. The spraying onto the leaves and the pouring on the roots were carried out once every 5 days. The amount of the treatment liquid that was sprayed onto the leaves is 50 mL per one time. Moreover, the amount of Treatment Liquid A that was poured on the roots is 50 mL per one time.

The Treatment Liquid A used was prepared in the same manner as described above by diluting the Treatment Liquid A stock solution with desalted distilled water such that the concentration of total Fe ions is 15 mg/L.

To the other 5 specimens (Specimens F to J), distilled water continued to be applied also after Day 61 under the same conditions as described above.

Figure 2:
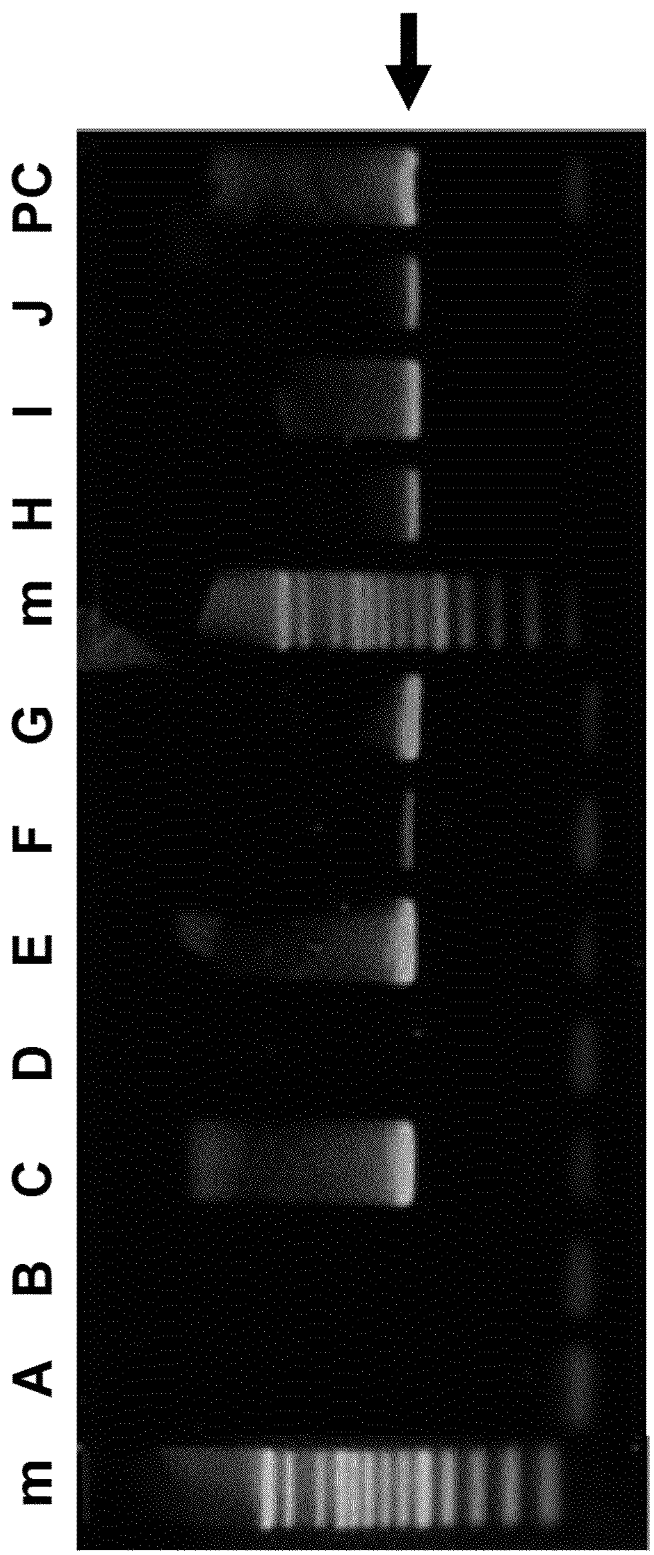
FIG. 2 shows the results of PCR diagnosis of specimens to which a treatment liquid was applied.
Figure 3A:
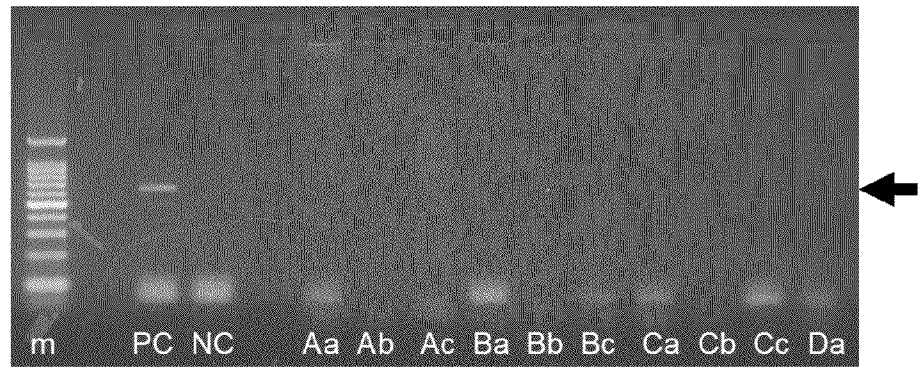
FIG. 3A to FIG. 3D show the results of PCR diagnosis of specimens to which the treatment liquid was applied.
Figure 3B:
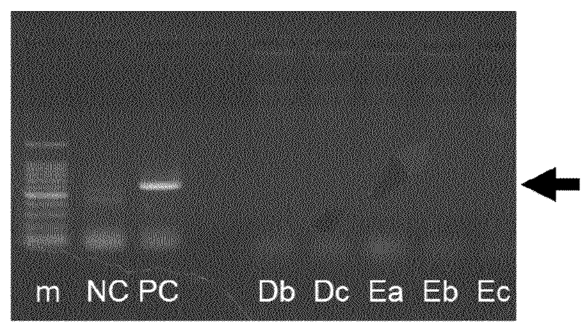
Figure 3C:
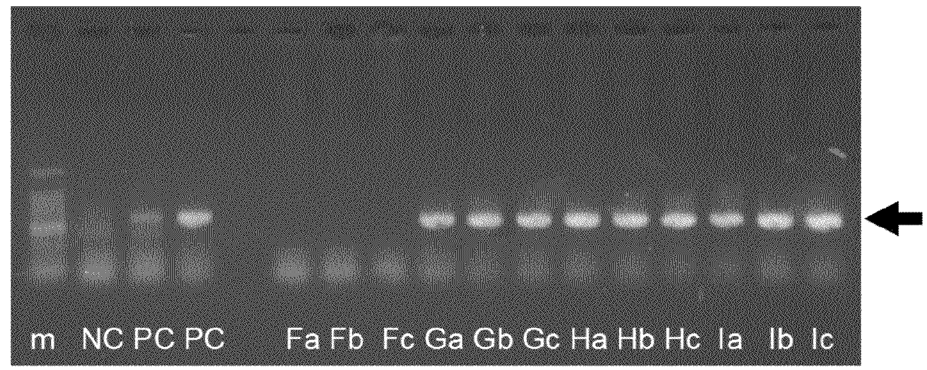
Figure 3D:
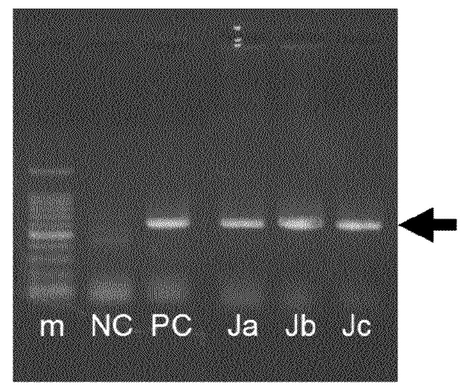

On Day 114 of the growing (Day 54 of the application of Treatment Liquid A), about 3 to 5 leaves of each specimen were picked, and the PCR diagnosis for each specimen was carried out in the same manner as described above. The results of the PCR diagnosis of the specimens to which Treatment Liquid A was applied and the specimens to which distilled water was applied are shown in FIG. 2 and Table 3. In addition, the band intensities of the individual specimens when taking the intensity of the positive band of PC as 100% are shown in Table 3. If the intensity of a positive band is 0%, then the result indicates that the specimen is not infected with HLB disease.

TABLE 3

| | Specimen | | | | | | | | | | |
|---|---|---|---|---|---|---|---|---|---|---|---|
| | PC | A | B | C | D | E | F | G | H | I | J |
| Band intensity (%) | 100 | 0 | 0 | 118 | 1 | 107 | 29 | 97 | 77 | 106 | 80 |

Among the specimens to which distilled water continued to be applied (Specimens F to J), in all the specimens, bands appeared at the same position as in PC (indicated by the arrow in the figure), and the condition of the disease had not been improved.

On the other hand, among the specimens to which Treatment Liquid A was applied (Specimens A to E), in 3 specimens (Specimens A, B and D), the positive bands disappeared, and the condition of the disease had been improved.

Also after Day 115, these specimens were further grown under the same conditions. On Day 252 of the growing (Day 192 of the application of the treatment liquid), about 5 leaves were picked from each of the upper part, the middle part and the lower part of each specimen, and the PCR diagnosis was carried out. The results of the PCR diagnosis of the specimens to which the treatment liquid was applied and the specimens to which distilled water was applied are shown in FIG. 3A to FIG. 3D and Table 4a to Table 4d.

In FIG. 3A to FIG. 3D, the results of the PCR diagnosis of leaves of the upper part, leaves of the middle part, and leaves of the lower part of Specimen A are described as Aa, Ab and Ac, respectively; and the results of the other specimens, Specimens B to J, in FIG. 3A to FIG. 3D are also described in the same manner. In the figure, NC represents a negative control, and, as the NC, a DNA sample that had been extracted from the leaves of a non-infected tree was used. In addition, the band intensities of the individual specimens when taking the intensity of the positive band of PC as 100% are shown in Table 4a to Table 4d).

TABLE 4a

| | Specimen | | | | | | | | | |
|---|---|---|---|---|---|---|---|---|---|---|
| | PC | Aa | Ab | Ac | Ba | Bb | Bc | Ca | Cb | Cc |
| Band intensity (%) | 100 | 0 | 0 | 0 | 0 | 0 | 0 | 0 | 0 | 0 |

TABLE 4b

| | Specimen | | | | | | |
|---|---|---|---|---|---|---|---|
| | PC | Da | Db | Dc | Ea | Eb | Ec |
| Band intensity (%) | 100 | 0 | 0 | 0 | 0 | 0 | 0 |

TABLE 4c

| | Specimen | | | | | | | | | |
|---|---|---|---|---|---|---|---|---|---|---|
| | PC | Fa | Fb | Fc | Ga | Gb | Gc | Ha | Hb | Hc |
| Band intensity (%) | 100 | 0 | 0 | 0 | 106 | 116 | 113 | 123 | 116 | 117 |

TABLE 4d

| | Specimen | | | | | | |
|---|---|---|---|---|---|---|---|
| | PC | Ia | Ib | Ic | Ja | Jb | Jc |
| Band intensity (%) | 100 | 110 | 131 | 101 | 84 | 86 | 91 |

Among the specimens to which distilled water continued to be applied (Specimens F to J), only in Specimen F, no band appeared at the same position as in PC; but, in all the other specimens, Specimens G to J, positive bands appeared at the same position as in PC (indicated by the arrow in the figure).

On the other hand, among the specimens to which the treatment liquid was applied (Specimens A to E), in all the specimens, no positive band appeared. Therefore, it is found that, in Specimens A to E, Citrus greening disease had been completely cured.

Figure 4:
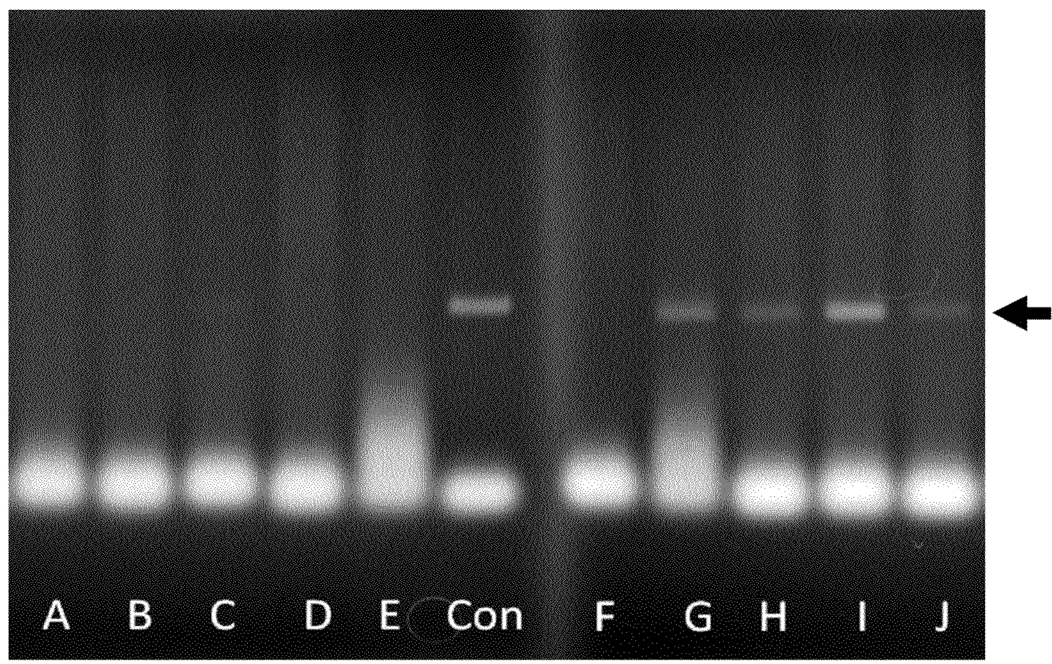
FIG. 4 shows the results of PCR diagnosis of specimens to which the treatment liquid was applied.

Also after Day 253, these specimens were further grown under the same conditions. One year and 9 months after the growing (1 year and 7 months after the application of the treatment liquid), about 3 to 5 leaves of each specimen were picked, and the PCR diagnosis for each specimen was carried out in the same manner as described above. The results of the PCR diagnosis of the specimens to which Treatment Liquid A or distilled water was applied are shown in FIG. 4. In addition, the band intensities of the individual specimens when taking the intensity of the positive band of PC as 100% are shown in Table 5.

TABLE 5

| | Specimen | | | | | | | | | | |
|---|---|---|---|---|---|---|---|---|---|---|---|
| | PC | A | B | C | D | E | F | G | H | I | J |
| Band intensity (%) | 100 | 0 | 0 | 4 | 0 | 0 | 0 | 65 | 42 | 139 | 37 |

Among the specimens to which distilled water continued to be applied (Specimens F to J), in 4 specimens (Specimens G to J), bands appeared at the same position as in PC (indicated by the arrow in the figure), and the condition of the disease had not been improved. In 1 specimen (Specimen F), the positive band disappeared. The cause thereof is not clear. However, since it has been known that some of individuals of Citrus greening disease bacteria become undetectable in rare cases, it is possible to think that the bacteria in Specimen F were one of such individuals.

On the other hand, among the specimens to which Treatment Liquid A was applied (Specimens A to E), in all the specimens, no band was detected at the same position as in PC (described as Con in the figure), and thereby it was confirmed that, in Specimens A to E, Citrus greening disease had been completely cured.

Thus, it was demonstrated that Citrus greening disease is able to be completely cured by applying Treatment Liquid A, which contains $Fe^{2+}$ ions, to a tree of rough lemon diseased with Citrus greening disease.

Figure 5:
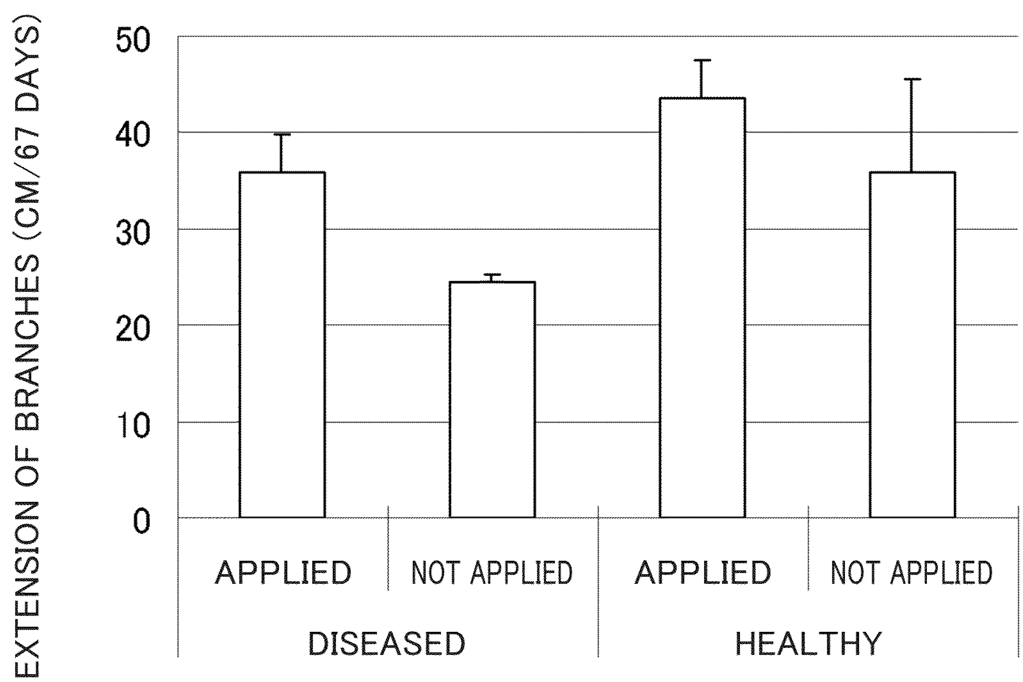
FIG. 5 shows extension of branches of specimens to which the treatment liquid was applied.

Further, the influence of the above Treatment Liquid A application on extension of branches of rough lemon was investigated. The branch lengths extended for 67 days are shown in FIG. 5. It was revealed that, when Treatment Liquid A had not been applied to trees diseased with Citrus greening disease, the extension of branches was about 25 cm; and, on the other hand, when Treatment Liquid A had been applied, the extension of branches was 35 cm or longer, and was equal to or longer than the extension of branches of healthy trees which were not diseased.

From the results as described above, it was demonstrated that application of Treatment Liquid A, which contains $Fe^{2+}$ ions, also has the effect of promoting extension of branches.

Thus, it was proved that the treatment liquid according to this embodiment has a surprising effect of allowing Citrus greening disease to be cured without impairing the growth of a citrus tree.

2. Effect on Tankan Orange

Figure 6A:
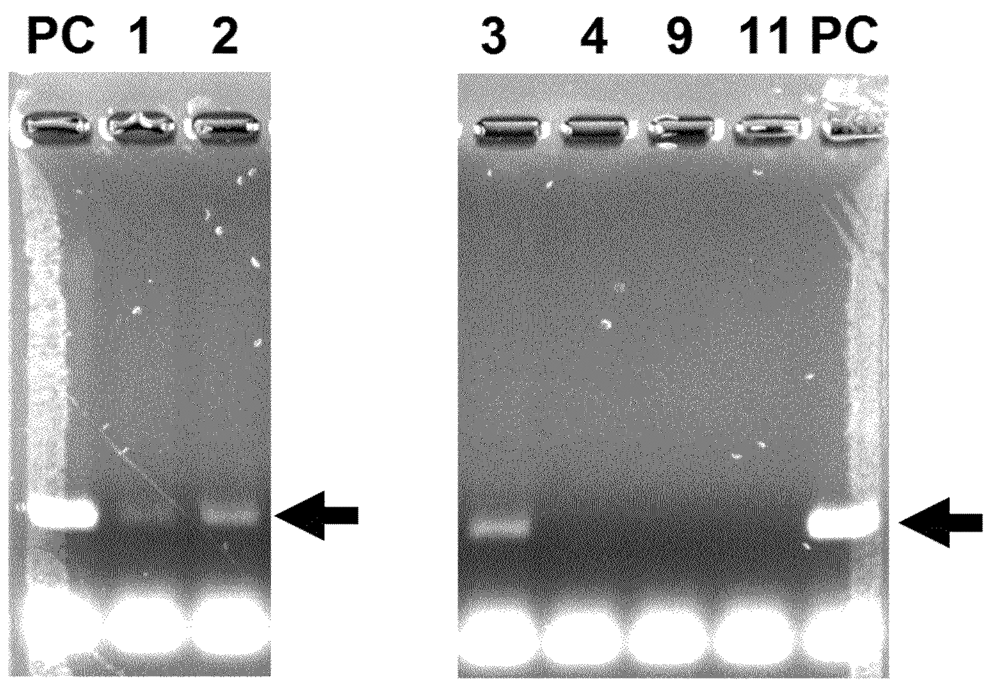
FIG. 6A and FIG. 6B show the results of PCR diagnosis of specimens to which a treatment liquid was applied.
Figure 6B:
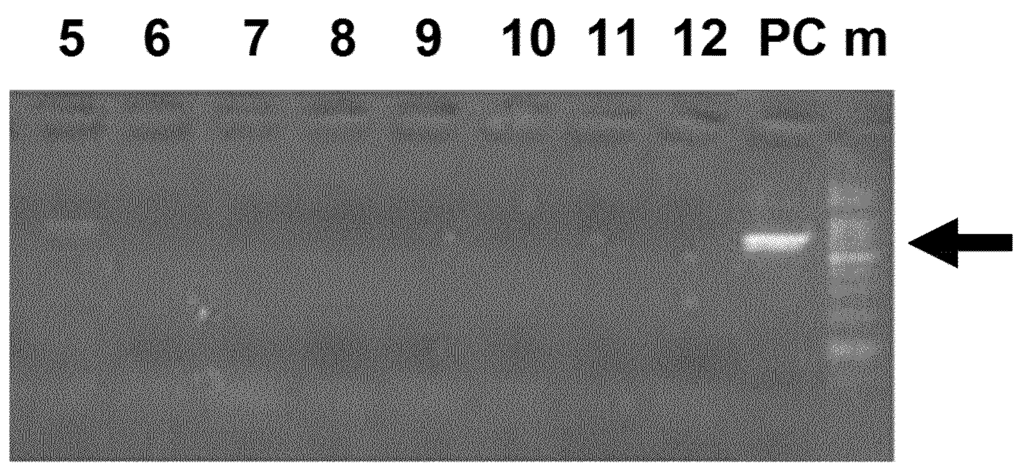

Next, evaluation using trees of tankan orange (*Citrus tankan* Hayata) as specimens was carried out. First, in order to identify trees diseased with Citrus greening disease from among plural trees of tankan orange at an orchard in Onna village, Okinawa prefecture, the PCR diagnosis as described above was carried out using old leaves of each tree. The results are shown in FIG. 6A and FIG. 6B, and Table 6a and Table 6b. The band intensities of the individual specimens when taking the intensity of the positive band of PC as 100% are shown in Table 6a and Table 6b.

TABLE 6a

| | Specimen | | | | | | |
|---|---|---|---|---|---|---|---|
| | PC | 1 | 2 | 3 | 4 | 9 | 11 |
| Band intensity (%) | 100 | 19 | 38 | 44 | 0 | 0 | 0 |

TABLE 6B

| Specimen | PC | 5 |
|---|---|---|
| Band intensity (%) | 100 | 10 |

As a result, as shown in FIG. 6A, in specimens represented by 1, 2 and 3 (Specimens 1 to 3), bands were detected at the same position as in PC, and thereby it was revealed that the specimens had been diseased with Citrus greening disease. Further, also in Specimen 5, the positive band of Citrus greening disease was detected as shown in FIG. 6B, and therefore Specimen 5 was also subjected to the following experiment as a specimen diseased with Citrus greening disease.

Treatment Liquid B whose concentration of total Fe ions is 30 mg/L was applied to these diseased specimens, Specimens 1 to 3; and Treatment Liquid A whose concentration of total Fe ions is 30 mg/L was applied to the diseased specimen, Specimen 5. The application of these treatment liquids was carried out by spraying Treatment Liquid B or Treatment Liquid A onto the leaves of the specimens. The spraying onto the leaves was carried out once every 7 days. The amounts of the treatment liquids that were sprayed onto the leaves are each 1.5 L per one time per one specimen. By spraying such a large amount of each treatment liquid onto the leaves, some of the sprayed treatment liquid will fall down to the soil, and therefore the same effect as in the pouring on the roots will be obtained.

The Treatment Liquid B used was prepared by diluting the Treatment Liquid B stock solution with desalted distilled water such that the concentration of total Fe ions is 30 mg/L. The Treatment Liquid A was prepared by diluting the Treatment Liquid A stock solution with desalted distilled water such that the concentration of total Fe ions is 30 mg/L.

Figure 7:
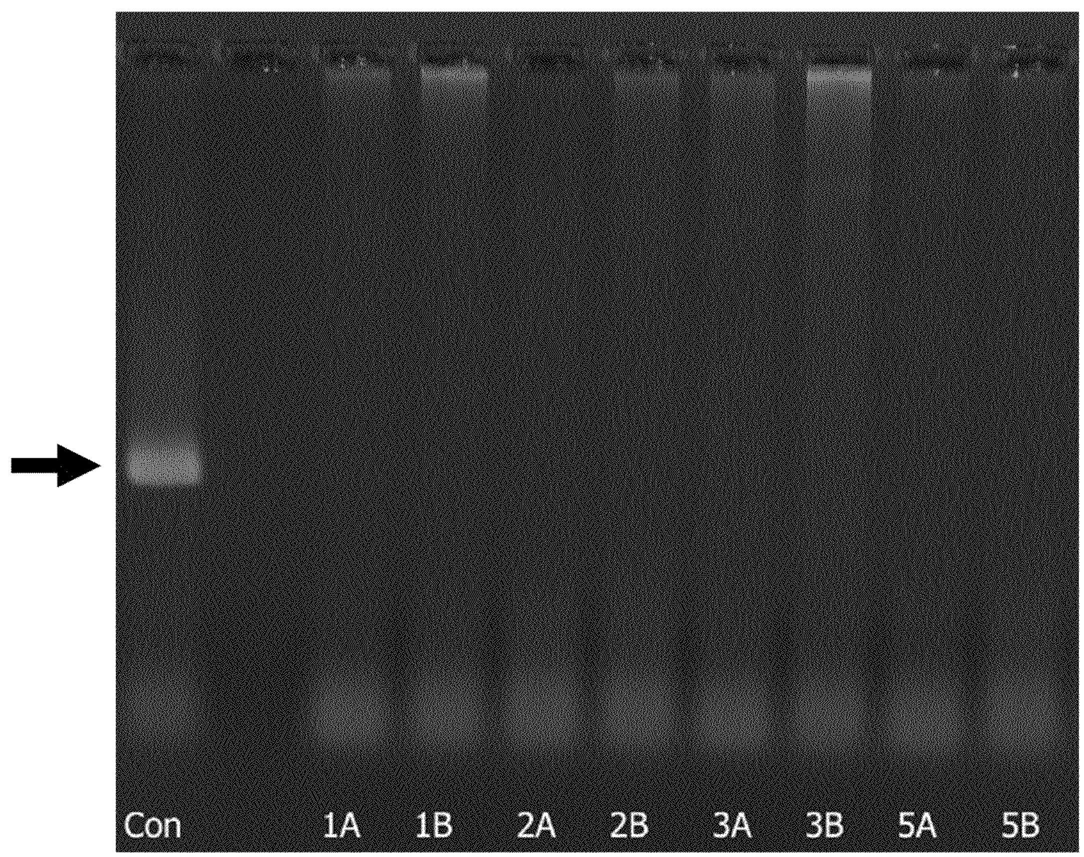
FIG. 7 shows the results of PCR diagnosis of specimens to which a treatment liquid was applied.

On Day 46 after the beginning of the treatment of the treatment liquids, 3 to 5 leaves were picked from each of new leaves and old leaves of each specimen; the DNAs were extracted in the same manner as described above; and the PCR diagnosis was carried out. The results are shown in FIG. 7 and Table 7. The band intensities of the individual specimens when taking the intensity of the positive band of PC as 100% are shown in Table 7.

TABLE 7

| | Specimen | | | | | | | | |
|---|---|---|---|---|---|---|---|---|---|
| | PC | 1A | 1B | 2A | 2B | 3A | 3B | 5A | 5B |
| Band intensity (%) | 100 | 0 | 0 | 0 | 0 | 0 | 0 | 0 | 0 |

In FIG. 7, A represents old leaves, and B represents new leaves. Among the specimens to which each treatment liquid was applied (Specimens 1 to 3, and 5), in all the specimens, no band was detected at the same position as in PC (described as Con in the figure), and thereby it was found that, in these specimens, Specimens 1 to 3, and 5, Citrus greening disease had been completely cured.

Thus, it was demonstrated that Treatment Liquid B and Treatment Liquid A, which contain $Fe^{2+}$ ions, are effective for curing Citrus greening disease also in tankan orange.

3. Effect on Shekwasha

Next, evaluation using trees of shekwasha (Citrus depressa Hayata) as specimens was carried out. Specimens infected with Citrus greening disease were prepared by inoculating the pathogenic bacteria from pathogenic trees by grafting in the same manner as in rough lemon described above.

The cultivation was carried out in a growth cabinet. The cultivation was carried out under the conditions a daytime temperature of 32° C. and a night temperature of 28° C. Nutrients were applied to the soil every 10 days. The applied nutrients were an aqueous solution that contains 10 mM calcium nitrate, 2.5 mM monopotassium dihydrogen phosphate, 2.5 mM magnesium sulfate heptahydrate and 1 mM potassium sulfate, and the solution was applied in an amount of 50 mL/one time per 1 pot.

To the specimens prepared as described above, the aqueous Fe-EDTA solution, Treatment Liquid B, the aqueous iron citrate solution and the aqueous iron sulfate solution whose concentrations of total Fe ions are 15 mg/L, and distilled water were respectively applied. Evaluation was carried out using 2 to 3 specimens for each aqueous Fe solution.

The above application of the aqueous Fe solutions and so on was carried out by spraying onto the leaves of the specimens and pouring on the roots of the specimens. The spraying onto the leaves and the pouring on the roots were respectively carried out once every 5 days. The amounts of the aqueous Fe solutions and so on that were sprayed onto the leaves are each 50 mL per one time. In addition, the amounts of the aqueous Fe solutions and so on that were poured on the roots are each 50 mL per one time.

On Day 309 after the beginning of the treatment of the aqueous Fe solutions, about 3 to 5 leaves of each specimen were picked; the DNAs were extracted and amplified by a PCR method; and the PCR diagnosis for Citrus greening disease was carried out. The mean values of the band intensities of the individual specimens when taking the intensity of the positive band of PC as 100% are shown in Table 8.

TABLE 8

| Specimen | PC | Aqueous Fe-EDTA solution | Treatment Liquid B | Aqueous iron citrate solution | Aqueous iron sulfate solution |
|---|---|---|---|---|---|
| Band intensity (%) | 100 | 127 | 43 | 70 | 76 |

As shown in Table 8, in the specimens to which the aqueous Fe-EDTA solution was applied, the band intensity was not decreased. On the other hand, in the specimens to which Treatment Liquid B, the aqueous iron citrate solution or the aqueous iron sulfate solution was applied, the band intensities were greatly decreased, and thereby it was found that HLB bacteria had been decreased and the condition of the disease had been improved.

Thus, it was demonstrated that the treatment liquid according to this embodiment is effective for curing Citrus greening disease also in shekwasha.

(Verification of Generation of Active Oxygen)

As described above, the treatment liquid according to this embodiment contains $Fe^{2+}$ ions. Accordingly, it is thought that, when the treatment liquid is applied to a tree, the $Fe^{2+}$ ions react with hydrogen peroxides generated within the cells to generate active oxygens. Therefore, the amounts of active oxygens generated by the various aqueous Fe solutions described above and the stability of the solutions were evaluated.

Active oxygens generated at the time when adding to distilled water the aqueous Fe solutions that had been respectively prepared in the above-described preparation of the aqueous Fe solutions for tests were measured by luminol reaction. Since distilled water contains a certain proportion of hydrogen peroxides, active oxygens are generated by addition of an aqueous solution containing $Fe^{2+}$ ions.

To 100 μL of each aqueous Fe solution, 50 μL of distilled water and 50 μL of a luminol solution were added, and the amount of the chemiluminescence was measured using Luminescencer (manufactured by ATTO Corporation) by integration for 10 seconds. The measurement of each sample was measured in triplicate. The greater the amount of active oxygens in the solution is, the higher the value of the luminescence intensity is.

The results are shown in FIG. 8. In FIG. 8, to 100 μL of each aqueous solution as described above, 50 μL of distilled water was added; 0, 60, 180 and 360 minutes later, 50 μL of a luminol solution was added; and the amount of the chemiluminescence was measured. In the aqueous Fe-EDTA solution, active oxygens were hardly detected as shown in FIG. 8. On the other hand, in the cases where Treatment Liquid A, Treatment Liquid B, the aqueous iron citrate solution or the aqueous iron sulfate solution was added to distilled water, strong luminescence intensity was detected, and thereby it was revealed that active oxygens had been generated. From these results, it was confirmed that $Fe^{2+}$ ions existed in Treatment Liquid A, Treatment Liquid B, the aqueous iron citrate solution and the aqueous iron sulfate solution.

Further, since active oxygens had been detected continuously for 3 hours or more after the addition of distilled water, it was proved that these aqueous solutions containing $Fe^{2+}$ ions are capable of stably holding $Fe^{2+}$ ions.

In order to identify active oxygen species generated by ferrous irons, 50 μL of distilled water containing 0 to 20 mM chlorogenic acid and 50 μL of a luminol solution were added to 100 μL of each aqueous Fe solution described above, and the luminescence intensity was measured in the same manner as described above.

Figure 9:
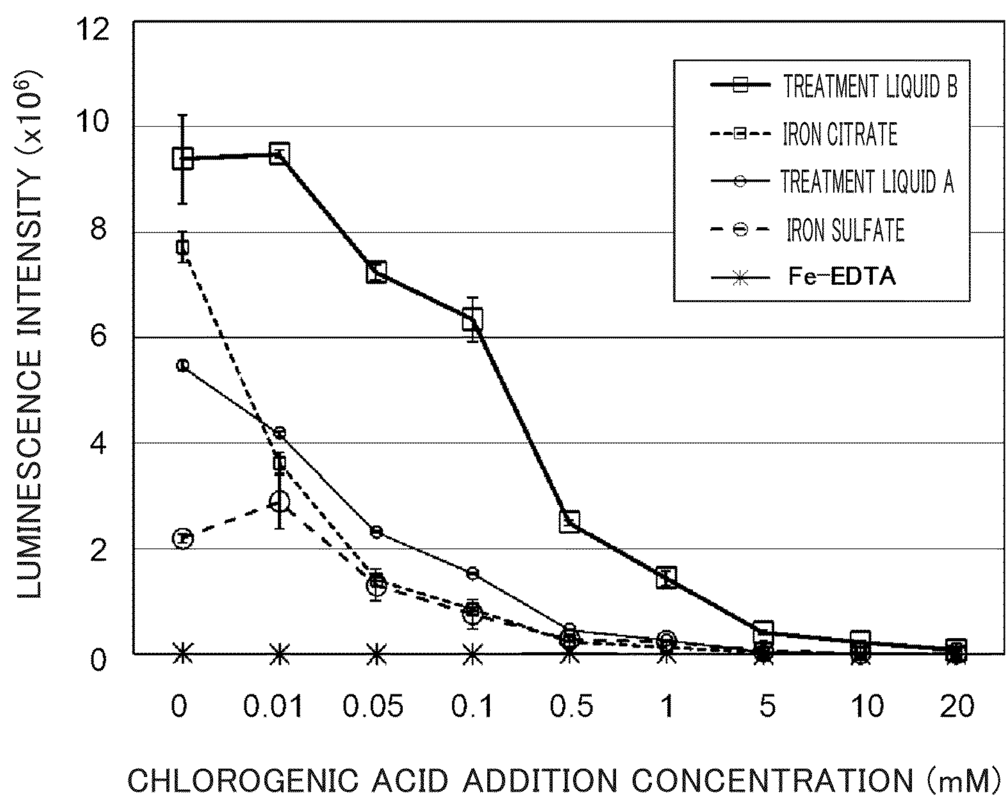
FIG. 9 shows the results obtained by measuring active oxygens by luminol reaction.

As a result, as shown in FIG. 9, in the samples to which a high concentration of chlorogenic acid was added, the value of the luminescence intensity was drastically decreased. Since chlorogenic acid has hydroxy radical scavenging property, the major component of active oxygens generated by addition of an aqueous Fe solution to distilled water was confirmed to be hydroxy radicals.

Even in the presence of the given concentrations of chlorogenic acid, the luminescence intensities were maintained to a certain extent in the aqueous Fe solutions other than the aqueous Fe-EDTA solution. Consequently, it was revealed that these aqueous Fe solutions are capable of supplying active oxygens stably and continuously even in the presence of a substance that scavenge or remove hydroxy radicals.

Figure 10A:
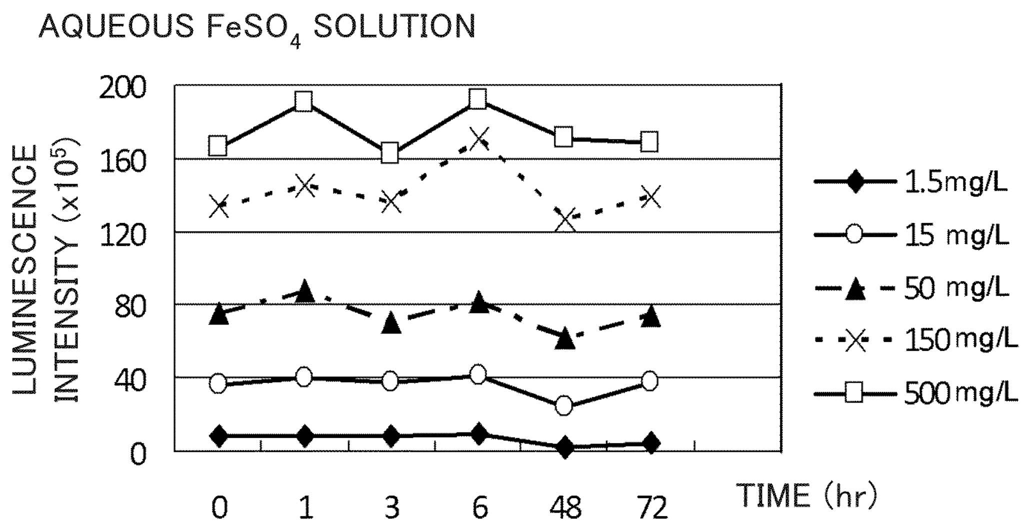
FIG. 10A and FIG. 10B show the results obtained by measuring active oxygens by luminol reaction.
Figure 10B:
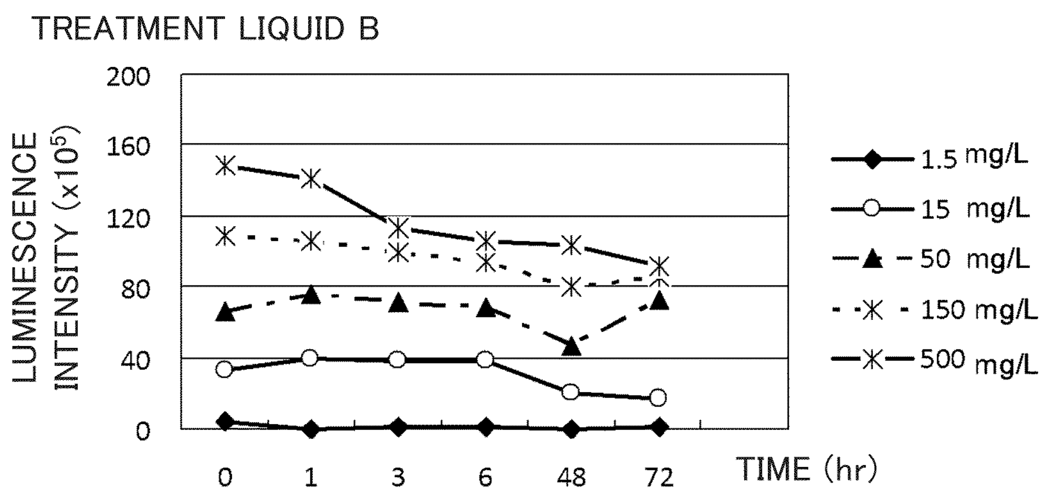

Next, for the aqueous iron sulfate solution and Treatment Liquid B, the relationship between the concentration of total Fe ions and the amount of active oxygens generated was investigated. As a result, as shown in FIG. 10A and FIG. 10B, in both of the aqueous iron sulfate solution and Treatment Liquid B, the luminescence intensities were low when the concentrations of total Fe ions were 1.5 mg/L, and thereby it was revealed that active oxygens are hardly generated. The 1.5 mg/L concentration of total Fe ions is a concentration that is generally applied as a fertilizer to a plant, and has no effect on Citrus greening disease. On the other hand, the luminescence intensities were $1\times10^7$ or more when the concentrations of total Fe ions were 150 mg/L or more, and thereby it was revealed that the amounts of active oxygens generated are very high. Therefore, it is thought that, if the concentration of total Fe ions is 150 mg/L or more, then a plant will be damaged by the excessive active oxygens.

From the results as described above, it was confirmed that the treatment liquid according to this embodiment contains $Fe^{2+}$ ions and is capable of stably holding $Fe^{2+}$ ions.

Thus, it was proved that the treatment liquid according to this embodiment contains $Fe^{2+}$ ions and has a surprising effect of allowing Citrus greening disease to be completely cured by application to citrus trees with Citrus greening disease.

In the present invention, it is considered that various embodiments and modifications are possible without departing from the broad spirit and scope of the present invention. The embodiments as described above are provided to illustrate the present invention and are not intended to limit the scope of the present invention.

The present application is based on Japanese patent application No. 2010-278654, filed on Dec. 14, 2010. The DESCRIPTION, CLAIMS and DRAWINGS of Japanese patent application No. 2010-278654 are incorporated herein by reference in their entirety.

INDUSTRIAL APPLICABILITY

As explained above, a citrus with Citrus greening disease is able to be cured by using the liquid for treatment of Citrus greening disease according to the present invention. Therefore, utilization of the present invention in the fields of agriculture in which citruses are cultivated is expected.

The invention claimed is:

1. A method of treating Citrus greening disease in a citrus plant comprising applying an effective amount of a liquid comprising Fe ions, wherein at least 18% by weight of the Fe ions are $Fe^{2+}$ ions, to leaves, a rhizosphere, or both, of a citrus plant infected with Citrus greening disease to decrease pathogenic bacteria in the citrus plant.

2. The method of treating Citrus greening disease according to claim 1, wherein the concentration of total Fe ions is from 10 mg/L to 100 mg/L.

3. The method of treating Citrus greening disease according to claim 2, wherein the liquid further contains an acid in addition to the total Fe ions.

4. The method of treating Citrus greening disease according to claim 3, wherein the acid is an organic acid.

5. The method of treating Citrus greening disease according to claim 4, wherein the organic acid comprises at least one of a carboxyl group and a hydroxyl group, and the total number of the carboxyl groups and the hydroxyl groups in the acid is two or more.

6. The method of treating Citrus greening disease according to claim 5, wherein the organic acid is at least one organic acid selected from the group consisting of citric acid, malic acid, tartaric acid, and ascorbic acid.

7. The method of treating Citrus greening disease according to claim 1, wherein the citrus plant is rough lemon, tankan orange or shekwasha.

* * * * *

```
                         SEQUENCE LISTING

<160> NUMBER OF SEQ ID NOS: 2

<210> SEQ ID NO 1
<211> LENGTH: 20
<212> TYPE: DNA
<213> ORGANISM: Candidatus Liberobacter

<400> SEQUENCE: 1

caccgaagat atggacaaca                                              20


<210> SEQ ID NO 2
<211> LENGTH: 21
<212> TYPE: DNA
<213> ORGANISM: Candidatus Liberobacter

<400> SEQUENCE: 2

caggttcttg tggtttttct g                                            21
```